US009297733B2

(12) United States Patent
Davis

(10) Patent No.: US 9,297,733 B2
(45) Date of Patent: Mar. 29, 2016

(54) DISPERSION COMPENSATION TECHNIQUE FOR DIFFERENTIAL SONAR MEASUREMENT—DENSITY METER

(75) Inventor: Michael A. Davis, Glastonbury, CT (US)

(73) Assignee: CiDRA Corporate Services Inc., Wallingford, CT (US)

( * ) Notice: Subject to any disclaimer, the term of this patent is extended or adjusted under 35 U.S.C. 154(b) by 682 days.

(21) Appl. No.: 13/583,274

(22) PCT Filed: Mar. 9, 2011

(86) PCT No.: PCT/US2011/027696
§ 371 (c)(1),
(2), (4) Date: Oct. 22, 2012

(87) PCT Pub. No.: WO2011/159375
PCT Pub. Date: Dec. 22, 2011

(65) Prior Publication Data
US 2013/0145842 A1    Jun. 13, 2013

Related U.S. Application Data

(60) Provisional application No. 61/312,038, filed on Mar. 9, 2010.

(51) Int. Cl.
*G01N 9/24*   (2006.01)
*G01F 1/66*   (2006.01)
*G01N 9/00*   (2006.01)
*G01N 11/00*  (2006.01)

(52) U.S. Cl.
CPC  *G01N 9/24* (2013.01); *G01F 1/663* (2013.01); *G01N 9/00* (2013.01); *G01N 2011/0073* (2013.01)

(58) Field of Classification Search
CPC ... G01F 1/663; G01N 9/24; G01N 2011/0073
See application file for complete search history.

(56) References Cited

U.S. PATENT DOCUMENTS

| | | | |
|---|---|---|---|
| 7,146,864 B2 | 12/2006 | Sullivan et al. |
| 7,152,003 B2 | 12/2006 | Loose et al. |
| 7,253,742 B2 | 8/2007 | Davis et al. |
| 7,330,797 B2 | 2/2008 | Bailey et al. |
| 7,400,985 B2 | 7/2008 | Fernald et al. |
| 7,474,966 B2 | 1/2009 | Fernald et al. |
| 7,503,227 B2 | 3/2009 | Davis et al. |
| 7,624,650 B2 | 12/2009 | Gysling et al. |
| 7,624,651 B2 | 12/2009 | Fernald et al. |
| 7,673,524 B2 | 3/2010 | Bailey et al. |
| 7,673,526 B2 | 3/2010 | Bailey et al. |
| 2003/0136186 A1 | 7/2003 | Gysling |
| 2004/0184350 A1 | 9/2004 | Brumley et al. |
| 2006/0053869 A1 | 3/2006 | Gysling et al. |
| 2006/0180349 A1 | 8/2006 | Dashevskiy |

*Primary Examiner* — Paul West

(57) ABSTRACT

The present invention provides a novel technique for canceling substantially the effects of dispersion when two speed of sound (SOS) measurements are required on the materials within a pipe to perform a calculation or derive certain characteristics about the materials flowing in the pipe. According to some embodiments of the present invention, the apparatus may comprise a signal processor configured to receive signals containing information about two speed of sound measurements having two sets of data related to materials within a pipe; and process the two sets of data simultaneously and determine a ridge point by point difference in order to cancel substantially effects of dispersion.

29 Claims, 7 Drawing Sheets

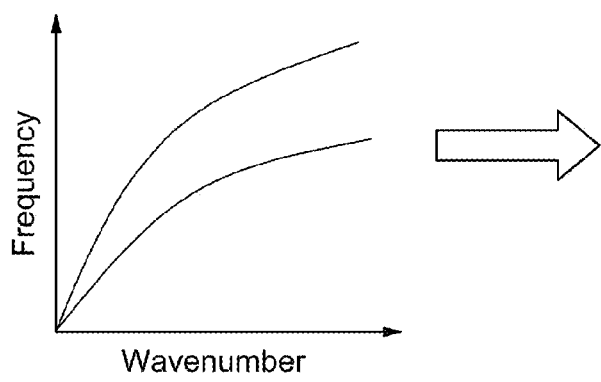
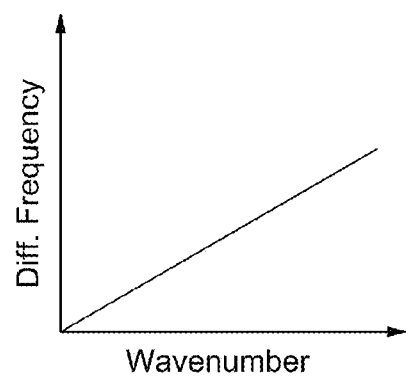
FIG. 2a
FIG. 2b

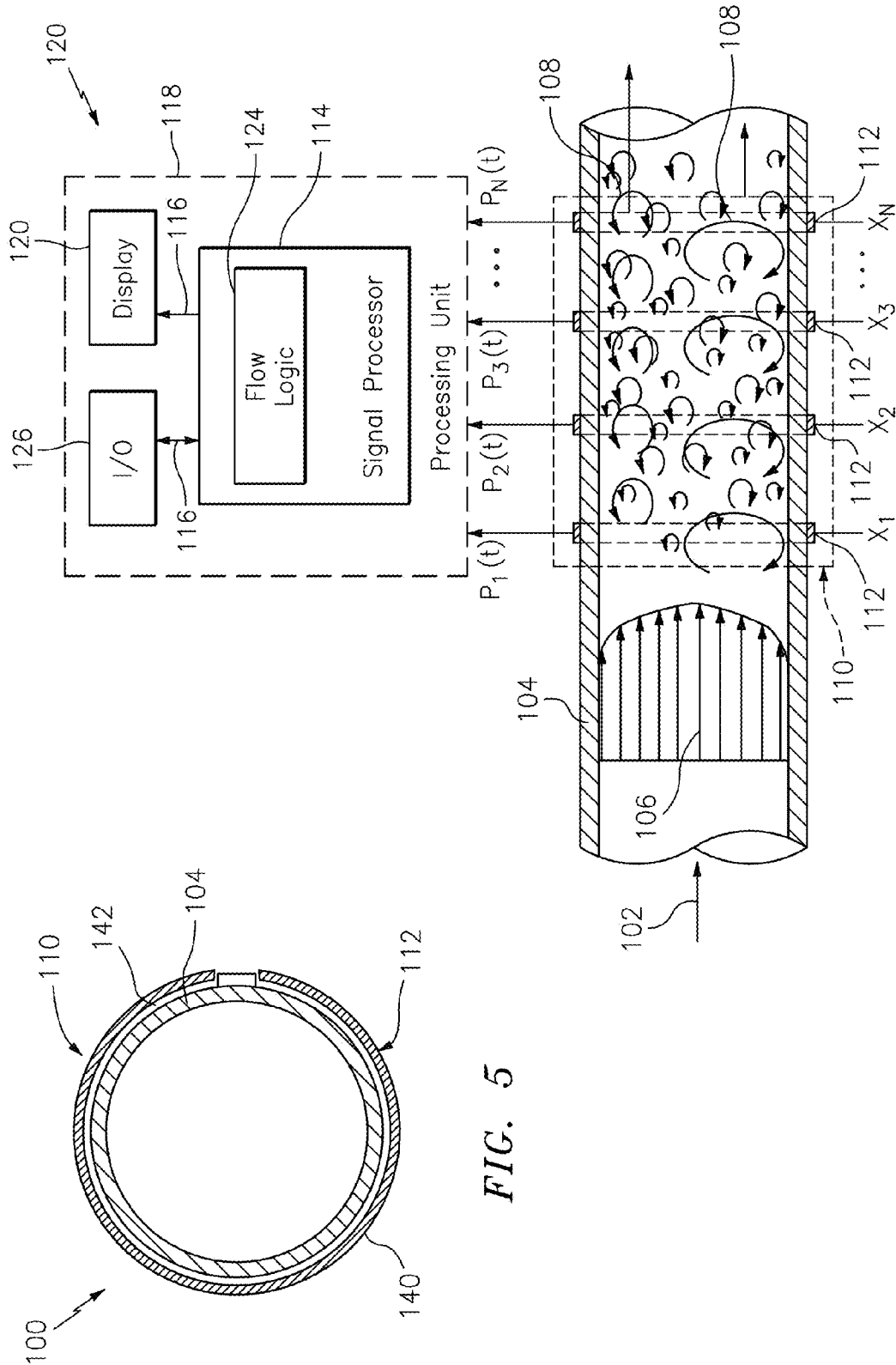

DISPERSION COMPENSATION TECHNIQUE FOR DIFFERENTIAL SONAR MEASUREMENT—DENSITY METER

CROSS-REFERENCE TO RELATED APPLICATIONS

The present application corresponds to international patent application serial no. PCT/US11/27696, filed 9 Mar. 2011, which claims the benefit of U.S. Provisional Patent Application No. 61/312,038, filed 9 Mar. 2010, which is incorporated by reference herein in its entirety.

BACKGROUND OF THE INVENTION

1. Technical Field

This invention relates generally to measuring a parameter of a fluid and more particularly to a method and apparatus for measuring a parameter of a fluid such as velocity and volumetric flow rate of the flow within a pipe.

2. Description of Related Art

A fluid flow process (flow process) includes any process that involves the flow of fluid through pipes, ducts, or other conduits, as well as through fluid control devices such as pumps, valves, orifices, heat exchangers, and the like. Flow processes are found in many different industries such as the oil and gas industry, refining, food and beverage industry, chemical and petrochemical industry, pulp and paper industry, power generation, pharmaceutical industry, and water and wastewater treatment industry. The fluid within the flow process may be a single phase fluid (e.g., gas, liquid or liquid/liquid mixture) and/or a multi-phase mixture (e.g. paper and pulp slurries or other solid/liquid mixtures). The multi-phase mixture may be a two-phase liquid/gas mixture, a solid/gas mixture or a solid/liquid mixture, gas entrained liquid or a three-phase mixture.

Currently, various sensing technologies exist for measuring various physical parameters of fluids in an industrial flow process. Such physical parameters may include, for example, velocity, volumetric flow rate, composition, gas volume fraction, consistency, density, and mass flow rate. One such sensing technology is described in U.S. Pat. No. 6,609,069 to Gysling, entitled "Method and Apparatus for Determining the Flow Velocity Within a Pipe", and U.S. Pat. No. 6,889,562, which are hereby incorporated herein by reference in their entirety. The '069 patent describes a method and corresponding apparatus for measuring the flow velocity of a fluid in an elongated body (pipe) by sensing vortical disturbances convecting with the fluid. The method includes the steps of providing an array of at least two sensors disposed at predetermined locations along the elongated body, wherein each sensor samples the pressure of the fluid at the position of the sensor at a predetermined sampling rate. The sampled data from each sensor at each of a number of instants of time spanning a predetermined sampling duration is accumulated and at least a portion of a so called k-ω plot is constructed from the accumulated sampled data, wherein the k-ω plot is indicative of a dispersion relation for the propagation of acoustic pressures emanating from the vortical disturbances. A convective ridge in the k-ω plot is identified and the orientation of the convective ridge in the k-ω plot is determined. The flow velocity based on a predetermined correlation of the flow velocity with the slope of the convective ridge of the k-ω plot may then be determined from this information. See also related technology disclosed in U.S. Pat. Nos. 7,673,524 and 7,895,903, which are hereby incorporated by reference.

For certain applications two speed of sound (SOS) measurements may be required on the materials within a pipe to perform a calculation or derive certain characteristics about the materials. An example would be a concept for a density meter where two SOS measurements are made on a material as it passes between two different pipes or sections of pipe that have different compliances. In this case, two SOS measurements are required with high precision to make an accurate density measurement. Of particular importance is the difference in the sound speed between the two measurements, as with all other parameters known, this is directly proportional to the density.

One of the primary issues with making an accurate SOS measurement is the correction for dispersion. Dispersion can arise from a variety of sources, but typically it can be due to the variance of the materials in the pipe such as varying particle sizes, densities or material mixtures in the pipe. This dispersion can manifest itself in the k-ω plane as a curved ridge.

FIG. 1a shows a typical SOS ridge in the k-ω plane without much dispersion. As can be seen, the ridges are basically straight and in this case a high quality SOS measurement can be made. FIG. 1b shows by the curved line what a ridge may follow in the case of dispersion. As seen, it can be difficult to determine the exact ridge location in the presence of dispersion.

SUMMARY OF THE INVENTION

In summary, the present invention provides a novel technique for canceling substantially the effects of dispersion when two speed of sound (SOS) measurements are required on the materials within a pipe to perform a calculation or derive certain characteristics about the materials flowing in the pipe.

According to some embodiments of the present invention, the apparatus may comprise a signal processor configured to receive signals containing information about two speed of sound measurements having two sets of data related to materials within a pipe; and process the two sets of data simultaneously and determine a ridge point by point difference in order to cancel substantially effects of dispersion.

The apparatus may also include one or more of the following features: The signal processor may be configured to receive the signals from two SONAR meters arranged in relation to the pipe, including for a density meter where the two SONAR meters arranged on two different pipes or two different sections of the pipe that have different compliances, including configured to use a differential calculation based at least partly on the fact that the same materials are passing through the two SONAR meters dispersion and dispersion characteristics should be similar. The signal processor may be configured to perform a point by point ridge subtraction in frequency so as to obtain a straightened differential k-ω plot of an acoustic ridge, including configured to use a simple line fit to calculate the difference in the speed of sound between the two speed of sound measurements, and configured to perform the simple line fit before a final speed of sound calculation is done, so that errors associated with each individual linear fits to separate ridges are eliminated and so that all common mode effects are eliminated between the two speed of sound measurements and a linear fit at the end can average out any different systematic noise on each signal or including configured to perform a calculation or derive certain characteristics about the materials, including a density measurement, based at least partly on the determination of the ridge point by the point difference. The signal processor may be configured to correct for dispersion due to a variance of the materials in the pipe, including varying particle size, densities or material mixtures in the pipe. The signal processor may be configured to correct for dispersion based at least partly on a relationship between the frequency (Hz) and a wavenumber (1/ft) related the signals received from two SONAR meters arranged in relation to the pipe. The signal processor may be configured to determine the difference in the speed of sound between the two speed of sound measurements, which is directly proportional to the density of the materials.

According to some embodiments of the present invention, the apparatus may take the form of, and/or may be implemented in, a density meter.

According to some embodiments of the present invention, the apparatus may comprise two SONAR meters arranged in relation to the pipe and configured to provide the signals containing information about two speed of sound measurements having two sets of data related to materials within a pipe for processing by the signal processor.

According to some embodiments of the present invention, the method may comprise steps for receiving in a signal processor signals containing information about two speed of sound measurements having two sets of data related to materials within a pipe; and processing the two sets of data simultaneously and determining a ridge point by point difference to cancel substantially effects of dispersion.

The method may also include one or more other steps set forth herein, including a step for receiving the signals from two SONAR meters arranged in relation to the pipe, including for a density meter where the two SONAR meters arranged on two different pipes or two different sections of the pipe that have different compliances; a step for using a differential calculation based at least partly on the fact that the same materials are passing through the two SONAR meters dispersion and dispersion characteristics should be similar; a step for performing a point by point ridge subtraction in frequency so as to obtain a straightened differential k-ω plot of an acoustic ridge; a step for using a simple line fit to calculate the difference in the speed of sound between the two speed of sound measurements; a step for performing the simple line fit before a final speed of sound calculation is done, so that errors associated with each individual linear fits to separate ridges are eliminated and so that all common mode effects are eliminated between the two speed of sound measurements and a linear fit at the end can average out any different systematic noise on each signal; a step for performing a calculation or derive certain characteristics about the materials, including a density measurement, based at least partly on the determination of the ridge point by the point difference; a step for correcting for dispersion due to a variance of the materials in the pipe, including varying particle size, densities or material mixtures in the pipe; a step for correcting for dispersion based at least partly on a relationship between the frequency (Hz) and a wavenumber (1/ft) related the signals received from two SONAR meters arranged in relation to the pipe; a step for determining the difference in the speed of sound between the two speed of sound measurements, which is directly proportional to the density of the materials.

According to some embodiments of the present invention, the method may comprise using the signal processor in a density meter, or arranging two SONAR meters in relation to the pipe that are configured to provide the signals containing information about two speed of sound measurements having two sets of data related to materials within a pipe for processing by the signal processor.

According to some embodiments of the present invention, the apparatus may comprise means for receiving in a signal processor signals containing information about two speed of sound measurements having two sets of data related to materials within a pipe; and means for processing the two sets of data simultaneously and determining a ridge point by point difference to cancel substantially effects of dispersion, consistent with that shown and described in the present invention.

Some advantages of the present invention include the fact that errors associated with each individual linear fits to separate ridges are eliminated, and all common mode effects are eliminate between the two and a linear fit at the end can average out any different systematic noise on each signal.

BRIEF DESCRIPTION OF THE DRAWING

Referring now to the drawing, the foregoing and other features and advantages of the present invention will be more fully understood from the following detailed description of illustrative embodiments, taken in conjunction with the accompanying drawing in which like elements are numbered alike:

FIG. 4 is schematic diagram of an apparatus known in the art for determining at least one parameter associated with a fluid flowing in a pipe using a known spatial sensor array.

FIG. 5 is a cross-sectional view of a pipe having a spatial sensor array arranged thereon.

DETAILED DESCRIPTION OF THE INVENTION

Figure 2:
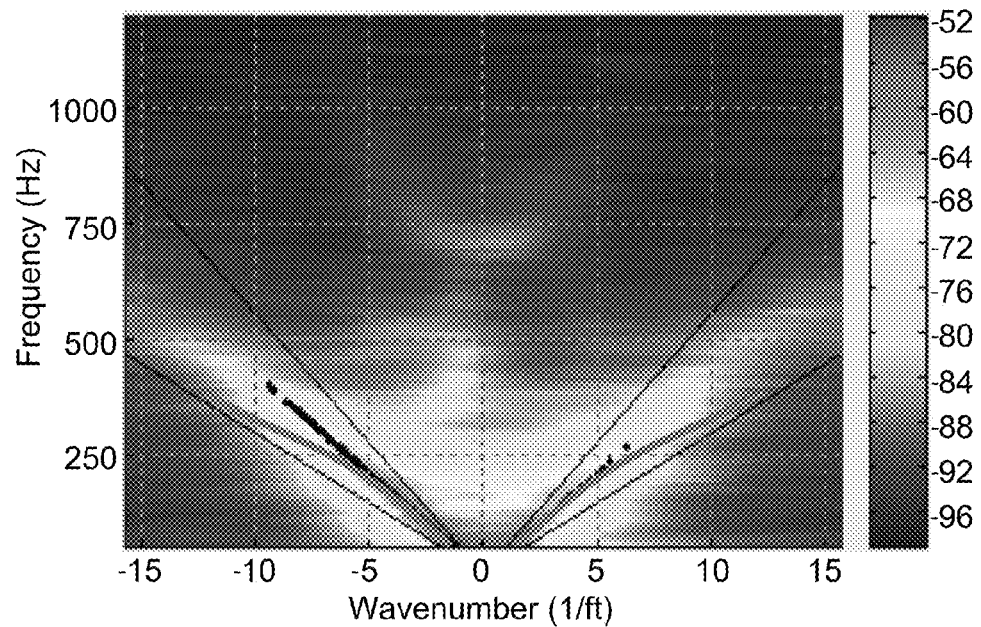
FIG. 2a shows a simple graph of frequency in relation to wavenumber which depicts what the combined processing in k-ω space of two SOS calculations with dispersion.
FIG. 2b shows a simple graph of frequency in relation to wavenumber which depicts a straightened differential k-ω plot if point by point ridge subtraction is performed in frequency.

In summary, the present invention provides a new and accurate technique that can be used to cancel the effects of dispersion when two SOS measurements are required, by processing two sets of data simultaneously and doing a ridge point by point difference. Since the same material is passing through both of the SONAR meters, the dispersion characteristics should be similar, permitting the use of a differential calculation. FIG. 2a shows what the combined processing in k-ω space of two SOS calculations with dispersion. As seen two ridges are present, one from each meter, each with a typical dispersion curve. FIG. 2b shows a straightened differential k-ω plot, after a point by point ridge subtraction is performed in frequency according to the present invention.

A simple line fit can now be used to calculate the difference in SOS between the two readings. Since this is performed before the final SOS calculation is done, the errors associated with each individual linear fits to the separate ridges are eliminated. In addition, all common mode effects are eliminate between the two and a linear fit at the end can average out any different systematic noise on each signal.

Figure 3A:
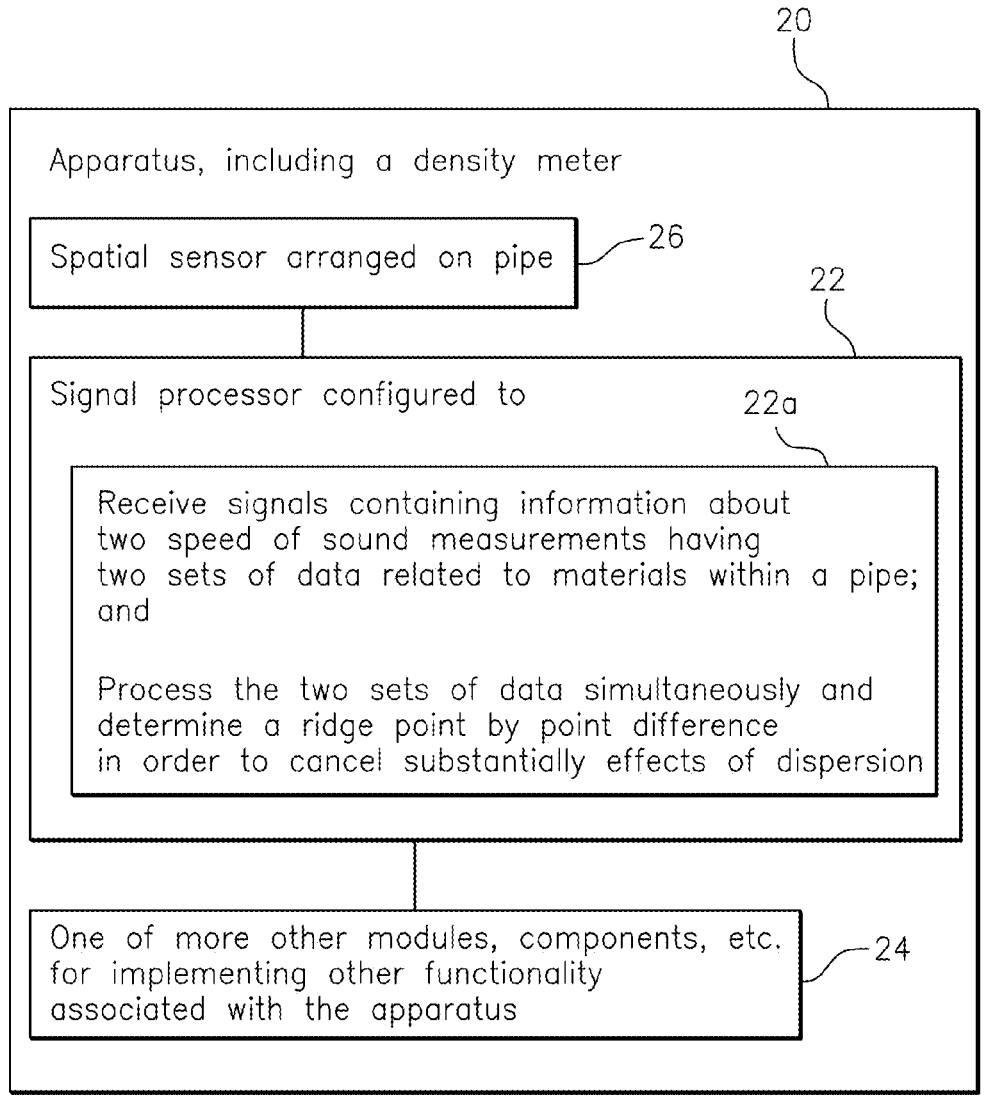
FIG. 3a is a block diagram of apparatus, including a signal processor, according to some embodiments the present invention.
Figure 3B:
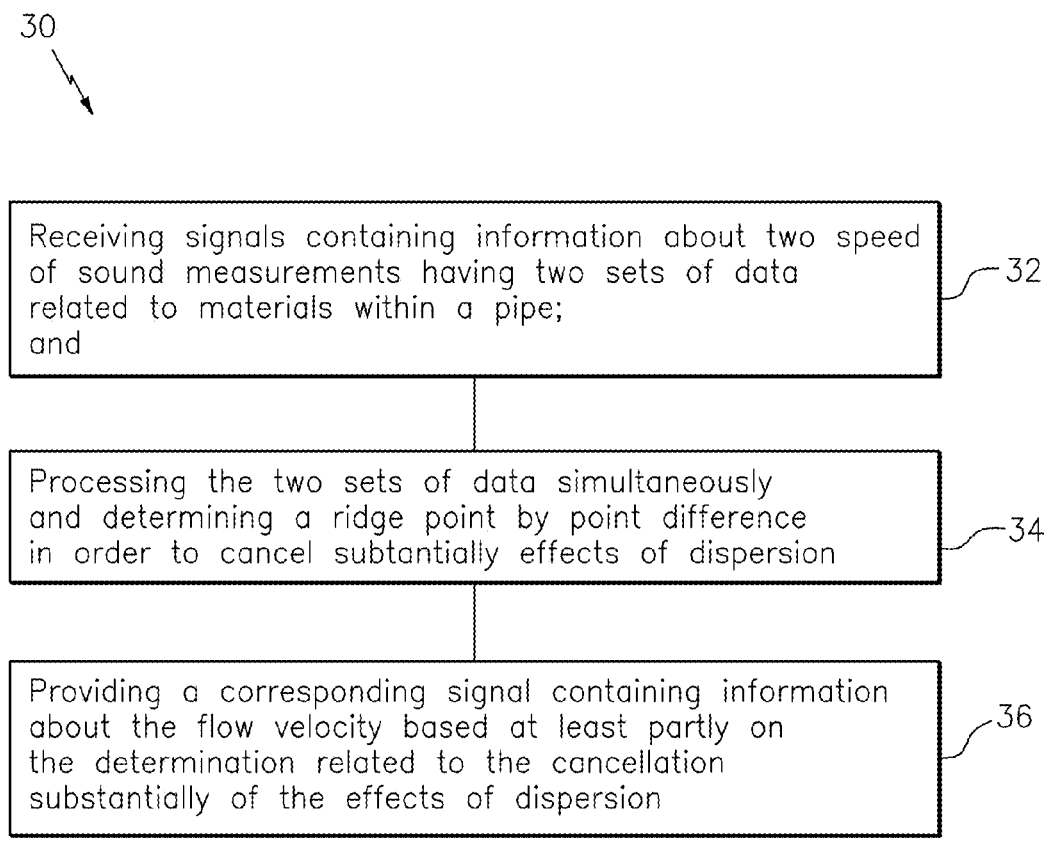
FIG. 3b is a block diagram of a flowchart of a method according to some embodiments the present invention.

FIGS. 3a and 3b

FIG. 3a shows an embodiment according to some embodiment of the present invention in the form of apparatus 20 comprising a signal processor 22 configured to receive signals containing information about two speed of sound measurements having two sets of data related to materials within a pipe; and process the two sets of data simultaneously and determine a ridge point by point difference in order to cancel substantially effects of dispersion, as shown in the signal processing block 22a. Once the ridge point by point difference is determined, then one or more parameters of the fluid such as velocity and volumetric flow rate of the flow within the pipe may be determined based at least partly by using the signal processing disclosed in, and consistent with that described in relation to, the known Gysling patents and other related patents identified and incorporated by reference herein, including by way of example those specifically naming the instant inventor, such as U.S. Pat. Nos. 7,503,227; 7,474,966; 7,400,985; 7,253,742; 7,152,003 and 7,146,864, as well as other U.S. Pat. Nos. 7,624,650; 7,624,651; 7,673,524; 7,673,526; and 7,330,797; which are all incorporated by reference in their entirety. The signals received by the signal processor 22 may take the form of signals provided by a spatial sensor 26, consistent with that shown and described in relation to FIGS. 4-7 herein. Alternatively, the signals received by the signal processor 22 may take the form of signals received and processed by some other signal processing device, e.g., a signal processing filtering or amplifying circuit, that are received from the spatial sensors shown and described in relation to FIGS. 4-7 herein.

By way of example, the functionality of the signal processor 22 may be implemented using hardware, software, firmware, or a combination thereof, for implementing the functionality of the signal processing block 22a, consistent with that described below in relation to FIGS. 4-7. In a typical software implementation, the signal processor 22 may include one or more microprocessor-based architectures having, e. g., at least one processor or microprocessor, random access memory (RAM) and/or read only memory (ROM), input/output devices and control, and data and address buses connecting the same, and/or at least one input processor and at least one output processor. A person skilled in the art would be able to program such a microcontroller (or microprocessor)-based implementation to perform the functionality described herein without undue experimentation. The scope of the invention is not intended to be limited to any particular implementation using technology either now known or later developed in the future. The scope of the invention is intended to include implementing the functionality of the signal processor as stand-alone processor or processor module, as separate processor or processor modules, as well as some combination thereof.

The apparatus 20 may also include one or more other modules, components, etc. generally indicated as 24 for implementing other functionality associated with the apparatus, but that does not form part of the underlying invention and is not described in detail, including modules or components for implementing input/output functionality, memory functionality and busing and address functionality associated with the processing of such the signal or signals received by the signal processor from the spirally wrapped sensor 10.

Figure 1:
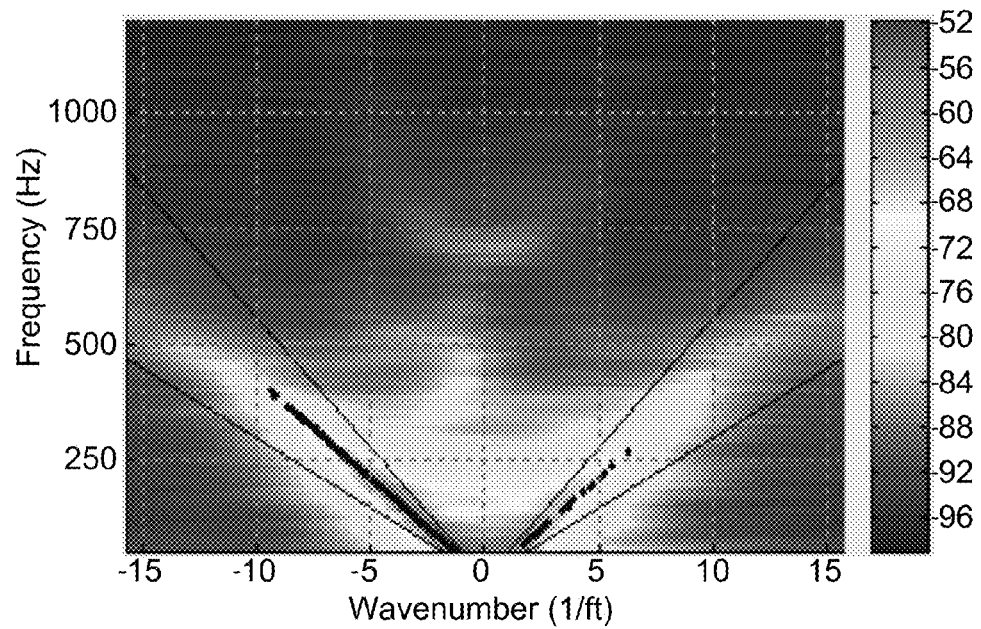
FIG. 1a shows a graph of frequency (Hz) in relation to wavenumber (1/ft) which depicts a typical SOS ridge in the k-co plane without much dispersion.
FIG. 1b shows a similar graph of frequency (Hz) in relation to wavenumber (1/ft) which depicts an SOS ridge in the k-ω plane with dispersion.

FIG. 3b shows a block diagram of a flowchart generally indicated as 30 having steps 32, 34, 36 for implementing a method for processing the signaling from the sensor shown in FIG. 1, according to some embodiments the present invention.

According to some embodiments of the present invention, the method may comprise a step 32 for receiving in a signal processor signals containing information about two speed of sound measurements having two sets of data related to materials within a pipe; and a step 34 for processing the two sets of data simultaneously and determining a ridge point by point difference to cancel substantially effects of dispersion.

The method may also comprise a step 38 for providing a corresponding signal containing information about one or more parameters related to the flow based at least partly on the determination related to the cancellation substantially of the effects of dispersion, including the flow velocity.

The method may also include one or more of the other features set forth above, including a step for receiving the signals from two SONAR meters arranged in relation to the pipe, including for a density meter where the two SONAR meters arranged on two different pipes or two different sections of the pipe that have different compliances; a step for using a differential calculation based at least partly on the fact that the same materials are passing through the two SONAR meters dispersion and dispersion characteristics should be similar; a step for performing a point by point ridge subtraction in frequency so as to obtain a straightened differential k-ω plot of an acoustic ridge; a step for using a simple line fit to calculate the difference in the speed of sound between the two speed of sound measurements; a step for performing the simple line fit before a final speed of sound calculation is done, so that errors associated with each individual linear fits to separate ridges are eliminated and so that all common mode effects are eliminated between the two speed of sound measurements and a linear fit at the end can average out any different systematic noise on each signal; a step for performing a calculation or derive certain characteristics about the materials, including a density measurement, based at least partly on the determination of the ridge point by the point difference; a step for correcting for dispersion due to a variance of the materials in the pipe, including varying particle size, densities or material mixtures in the pipe; a step for correcting for dispersion based at least partly on a relationship between the frequency (Hz) and a wavenumber (1/ft) related the signals received from two SONAR meters arranged in relation to the pipe; a step for determining the difference in the speed of sound between the two speed of sound measurements, which is directly proportional to the density of the materials.

Example of the Known Signal Processing Technology

By way of example, FIGS. 4-7 disclose known signal processing technology disclosed in U.S. Pat. No. 6,609,069 and U.S. Pat. No. 6,889,562, each of which are incorporated herein by reference in their entireties, related to unsteady pressures along a pipe caused by coherent structures (e.g., turbulent eddies and vortical disturbances) that convect with a fluid flowing in the pipe contain useful information regarding parameters of the fluid, where the unsteady pressures along the pipe are sensed using a spatial array 110 of at least two sensors 112 shown in FIG. 4. FIG. 4 shows apparatus for measuring the velocity and/or volumetric flow of a fluid flowing within a pipe that is also similar to that described, by way of example, in U.S. Pat. No. 7,400,985; U.S. Pat. No. 7,673, 524; U.S. Pat. No. 7,895,903, as well as U.S. patent application Ser. No. 10/712,833, filed on Nov. 12, 2003, now abandoned, which are all hereby incorporated herein by reference. The present invention described in relation to FIGS. 2a-2b above provides various new means for using this underlying signal processing technology to measure parameters of a fluid flow, such as, for example, velocity and volumetric flow rate as shown and described in relation to FIGS. 4-7, based at least partly on the use of a dispersion compensation technique consistent with that as described in relation to FIGS. 2a-2b that may be used as a part of the signal processing described in relation to the spatial array 110 of the at least two sensors 112 shown in FIG. 4.

In FIG. 4, the known apparatus 100 measures at least one parameter associated with a flow 102 flowing within a duct, conduit or other form of pipe 104, wherein the parameter of the flow 102 may include, for example, at least one of the velocity of the flow 102 and the volumetric flow rate of the flow 102. The flow 102 is shown passing through the pipe 104, wherein the flow 102 is depicted as a non-stratified, Newtonian flow operating in the turbulent regime at Reynolds numbers above about 100,000. The flow 102 has a velocity profile 106 that is uniformly developed from the top of the pipe 104 to the bottom of the pipe 104. Furthermore, the coherent structures 108 in the non-stratified, turbulent, Newtonian flow 102 exhibit very little dispersion. In other words, the speed of convection of the coherent structures 108 is not strongly dependent on the physical size of the structures 108. It should be appreciated that, as used herein, dispersion describes the dependence of convection velocity with wavelength, or equivalently, with temporal frequency. It should also be appreciated that flows for which all wavelengths convect at a constant velocity are termed "non-dispersive" and for turbulent, Newtonian flow, there is typically not a significant amount of dispersion over a wide range of wavelength to diameter ratios.

While the flow 102 is depicted as having a uniform velocity profile, it should be appreciated that the present invention may be used to measure stratified flows 102. Stratified flow 102 has a velocity profile 106 that is skewed from the top of the pipe 104 to the bottom of the pipe 104, as may be found in industrial fluid flow processes involving the transportation of a high mass fraction of high density, solid materials through a pipe 104 where the larger particles travel more slowly at the bottom of the pipe 104. For example, the flow 102 may be part of a hydrotransport process.

The apparatus 100 of FIG. 4 measures parameters such as velocity and volumetric flow rate of a stratified flow and/or non-stratified flow 102, wherein the apparatus 100 may include a spatial array 110 of at least two sensors 112 disposed at different axial locations $x_1 \ldots x_N$ along the pipe 104. Each of the sensors 112 provides a pressure signal P(t) indicative of unsteady pressure created by coherent structures convecting with the flow 102 within the pipe 104 at a corresponding axial location $x_1 \ldots x_N$ of the pipe 104. The pressure generated by the convective pressure disturbances (e.g., eddies 108) may be measured through strained-based sensors 112 and/or pressure sensors 112. The sensors 112 provide analog pressure time-varying signals $P_1(t), P_2(t), P_3(t) \ldots P_N(t)$ to a signal processor 114, which determines the parameter of the flow 102 using pressure signals from the sensors 112, and outputs the parameter as a signal 116.

While the apparatus 100 is shown as including four sensors 112, it is understood that the array 110 of sensors 112 may include two or more sensors 112, each providing a pressure signal P(t) indicative of unsteady pressure within the pipe 104 at a corresponding axial location X of the pipe 104. Generally, the accuracy of the measurement improves as the number of sensors 112 in the array 110 increases. Thus, the degree of accuracy provided by the greater number of sensors 112 is offset by the increase in complexity and time for computing the desired output parameter of the flow 102 and the number of sensors 112 used is dependent at least in part on the degree of accuracy desired and the desire update rate of the output parameter provided by the apparatus 100.

The signals $P_1(t) \ldots P_N(t)$ provided by the sensors 112 in the array 110 are processed by the signal processor 114, which may be part of a larger processing unit 118. For example, the signal processor 114 may be a microprocessor and the processing unit 118 may be a personal computer or other general purpose computer. It is contemplated that the signal processor 114 may be any one or more analog or digital signal processing devices for executing programmed instructions, such as one or more microprocessors or application specific integrated circuits (ASICS), and may include memory for storing programmed instructions, set points, parameters, and for buffering or otherwise storing data.

The signal processor 114 may output the one or more parameters 116 to a display 120 or another input/output (I/O) device 122. The I/O device 122 may also accept user input parameters. The I/O device 122, display 120, and signal processor 114 unit may be mounted in a common housing, which may be attached to the array 110 by a flexible cable, wireless connection, or the like. The flexible cable may also be used to provide operating power from the processing unit 118 to the array 110 if necessary.

Figure 6:
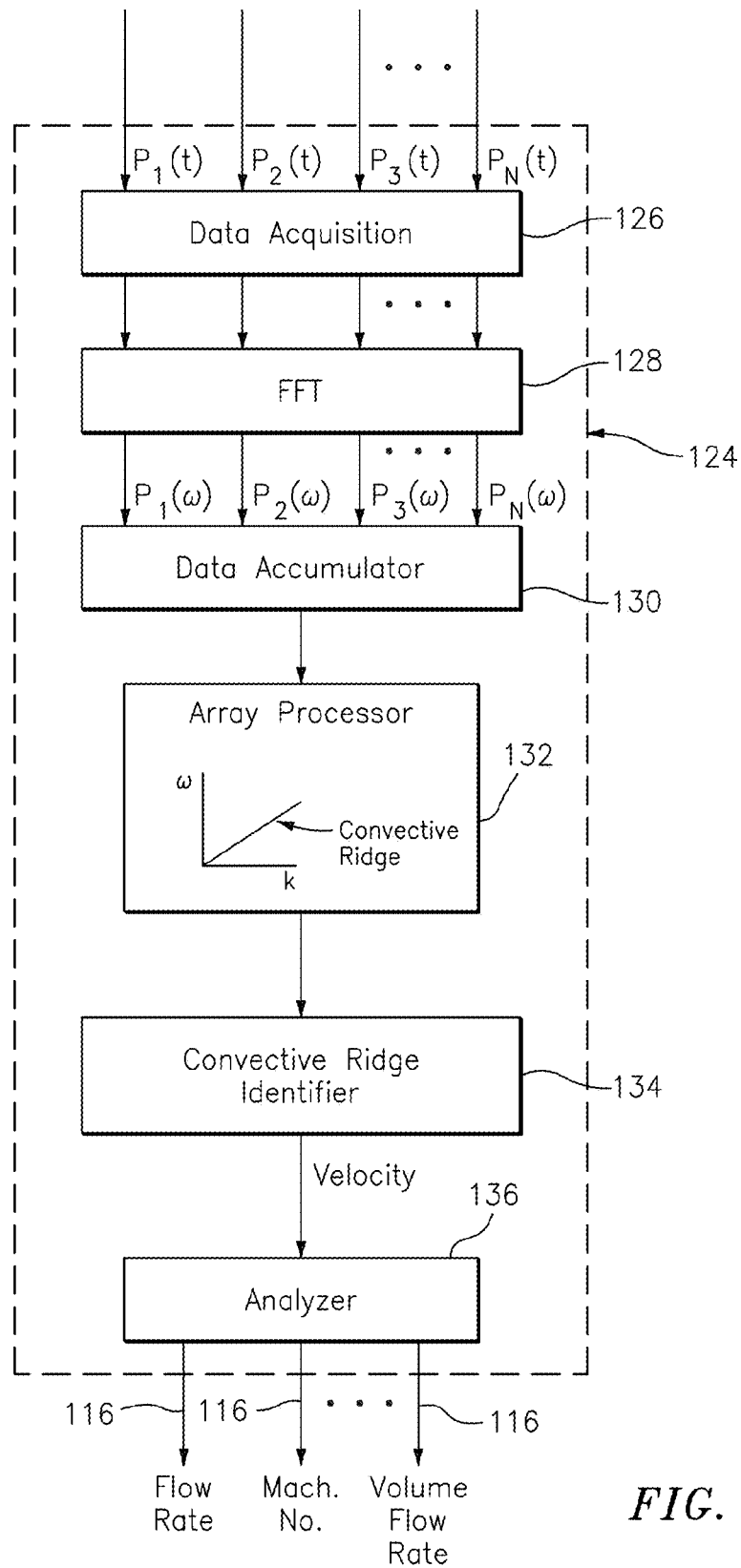
FIG. 6 is a block diagram of a flow logic known in the art.

To determine the one or more parameters 116 of the flow 102, the signal processor 114 applies the data from the sensors 112 to flow logic 124 executed by the signal processor 114. Referring to FIG. 6, an example of flow logic 124 is shown. Some or all of the functions within the flow logic 124 may be implemented in software (using a microprocessor or computer) and/or firmware, or may be implemented using analog and/or digital hardware, having sufficient memory, interfaces, and capacity to perform the functions described herein.

The flow logic 124 may include a data acquisition unit 126 (e.g., A/D converter) that converts the analog signals $P_1(t) \ldots P_N(t)$ to respective digital signals and provides the digital signals $P_1(t) \ldots P_N(t)$ to FFT logic 128. The FFT logic 128 calculates the Fourier transform of the digitized time-based input signals $P_1(t) \ldots P_N(t)$ and provides complex frequency domain (or frequency based) signals $P_1(\omega), P_2(\omega), P_3(\omega), \ldots P_N(\omega)$ indicative of the frequency content of the input signals. Instead of FFT's, any other technique for obtaining the frequency domain characteristics of the signals $P_1(t)$-$P_N(t)$, may be used. For example, the cross-spectral density and the power spectral density may be used to form a frequency domain transfer functions (or frequency response or ratios) discussed hereinafter.

Figure 7:
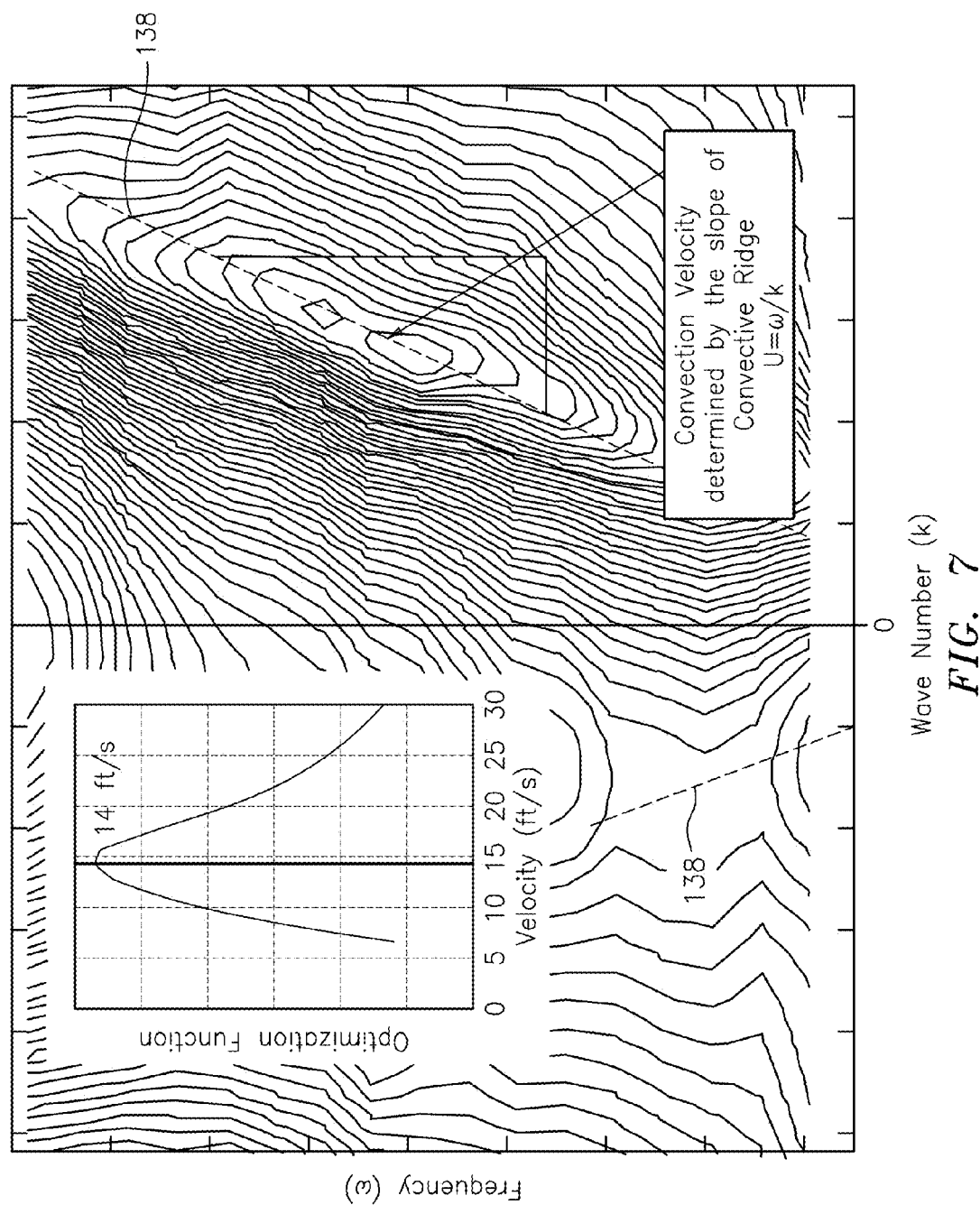
FIG. 7 is a k-ω plot of data processed from an apparatus known in the art that illustrates the slope of the convective ridge, and a plot of the optimization function of the convective ridge.

One technique of determining the convection velocity of the coherent structures (e.g., turbulent eddies) 108 within the flow 102 is by characterizing a convective ridge of the resulting unsteady pressures using an array of sensors or other beam forming techniques, similar to that disclosed U.S. Pat. No. 6,609,069, which is incorporated herein by reference in its entirety. A data accumulator 130 accumulates the frequency signals $P_1(\omega)$-$P_N(\omega)$ over a sampling interval, and provides the data to an array processor 132, which performs a spatial-temporal (two-dimensional) transform of the sensor data, from the x-t domain to the k-$\omega$ domain, and then calculates the power in the k-$\omega$ plane, as represented by a k-$\omega$ plot (FIG. 7).

The array processor 132 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$, where $\lambda$ is the wavelength of a spectral component, and corresponding angular frequencies given by $\omega=2\pi v$.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter convecting with a flow are time stationary and have a coherence length long enough that it is practical to locate sensors 112 apart from each other and yet still be within the coherence length.

Convective characteristics or parameters have a dispersion relationship that can be approximated by the straight-line equation, $$k=\omega/u, \quad\quad\quad\quad\quad\quad\quad\quad\quad\quad\quad\quad\text{(Eqn. 1)}$$

where u is the convection velocity (flow velocity). A plot of k-$\omega$ pairs obtained from a spectral analysis of sensor samples associated with convective parameters portrayed so that the energy of the disturbance spectrally corresponding to pairings that might be described as a substantially straight ridge, a ridge that in turbulent boundary layer theory is called a convective ridge. As will be described hereinafter, as the flow becomes increasingly dispersive, the convective ridge becomes increasingly non-linear. What is being sensed are not discrete events of coherent structures 108, but rather a continuum of possibly overlapping events forming a temporally stationary, essentially white process over the frequency range of interest. In other words, the convective coherent structures 108 are distributed over a range of length scales and hence temporal frequencies.

To calculate the power in the k-$\omega$ plane, as represented by a k-$\omega$ plot (see FIG. 7) of either the signals, the array processor 132 determines the wavelength and so the (spatial) wavenumber k, and also the (temporal) frequency and so the angular frequency $\omega$, of various of the spectral components of the stochastic parameter. There are numerous algorithms available in the public domain to perform the spatial/temporal decomposition of arrays of sensors 112. It should be appreciated that the present embodiment may use temporal and spatial filtering to precondition the signals to effectively filter out the common mode characteristics Pcommon mode and other long wavelength (compared to the sensor spacing) characteristics in the pipe 104 by differencing adjacent sensors 112 and retain a substantial portion of the stochastic parameter associated with the flow field and any other short wavelength (compared to the sensor spacing) low frequency stochastic parameters.

In the case of suitable coherent structures 108 being present, the power in the k-$\omega$ plane shown in a k-$\omega$ plot of FIG. 7 shows a convective ridge 138. The convective ridge represents the concentration of a stochastic parameter that convects with the flow and is a mathematical manifestation of the relationship between the spatial variations and temporal variations described above. Such a plot will indicate a tendency for k-$\omega$ pairs to appear more or less along a line 138 with some slope, the slope indicating the flow velocity.

Once the power in the k-$\omega$ plane is determined, a convective ridge identifier 134 uses one or another feature extraction method to determine the location and orientation (slope) of any convective ridge 138 present in the k-$\omega$ plane. For example, in one embodiment, a so-called slant stacking method is used, a method in which the accumulated frequency of k-$\omega$ pairs in the k-$\omega$ plot along different rays emanating from the origin are compared, each different ray being associated with a different trial convection velocity (in that the slope of a ray is assumed to be the flow velocity or correlated to the flow velocity in a known way). The convective ridge identifier 134 provides information about the different trial convection velocities, information referred to generally as convective ridge information. An analyzer 136 examines the convective ridge information including the convective ridge orientation (slope) and assuming the straight-line dispersion relation given by $k=\omega/u$, the analyzer 136 determines the flow velocity and/or volumetric flow, which are output as parameters 116. The volumetric flow may be determined by multiplying the cross-sectional area of the inside of the pipe 104 with the velocity of the process flow 102.

As previously noted, for turbulent, Newtonian fluids, there is typically not a significant amount of dispersion over a wide range of wavelength to diameter ratios. As a result, the convective ridge 138 in the k-$\omega$ plot is substantially straight over a wide frequency range and, accordingly, there is a wide frequency range for which the straight-line dispersion relation given by $k=\omega/u$ provides accurate flow velocity measurements. For stratified flows, however, some degree of dispersion exists such that coherent structures 108 convect at velocities which depend on their size. As a result of increasing levels of dispersion, the convective ridge 138 in the k-$\omega$ plot becomes increasingly non-linear. Thus, unlike the non-dispersive flows, determining the flow rate of a dispersive mixture by tracking the speed at which coherent structures 108 convect requires a methodology that accounts for the presence of significant dispersion, as described in greater detail in U.S. patent application Ser. No. 11/077,709, filed on Mar. 10, 2005, which is incorporated herein by reference.

In the embodiment shown in FIG. 4 and FIG. 5, each of the sensors 112 is formed by a strip of piezoelectric material 140 such as, for example, the polymer, polarized fluoropolymer, PVDF, which measures the strain induced within the pipe 104 due to the coherent structures convecting with the flow 102, similar to that described in U.S. patent application Ser. No. 10/712,818 and U.S. Provisional patent application Ser. No. 10/712,833, which are incorporated herein by reference. The sensors 112 can be formed from PVDF films, co-polymer films, or flexible PZT sensors, similar to that described in "Piezo Film Sensors technical Manual" provided by Measurement Specialties, Inc. of Fairfield, N.J., which is incorporated herein by reference. The PVDF sensors include PVDF material disposed between a pair of conductive layers. The conductive layers are electrically connected to a processor by a pair of twisted wires, wherein the conductive layer may be formed of silver ink. The strips of piezoelectric film material forming the sensors 112 along each axial location $x_1 \ldots x_N$ of the pipe 104 may be adhered to the surface of a steel strap 142 (e.g., a hose clamp) that extends around and clamps onto the outer surface of the pipe 104. As discussed hereinafter, other types of sensors 112 and other methods of attaching the sensors 112 to the pipe 104 may be used.

As shown in FIG. 5, the PVDF material 140 of each sensor 112 is disposed substantially around the circumference of the pipe 104, which enables the sensing material 140 to measure pressure disturbances attributed to the convective vortices 106 propagating with the fluid flow 102. The configuration of the sensing material being disposed substantially around the circumference of the pipe 104 filters out pressure disturbances associated with vibration and other bending modes of the pipe 104. Unfortunately, the sensors 112 also sense unsteady pressure attributed to acoustic pressures or noise within the pipe 104, wherein the measurement of these acoustic pressures decreases the signal to noise ratio when measuring the convective turbulence 106.

In the geometry of the sensors 112 (in FIG. 5), asymmetric bending modes create equal and opposite deformation of the sensor 112 and therefore create no signal. Acoustic modes create a uniform distortion, and therefore create a signal along with a signal associated with vortical disturbances. (One might expect the acoustic signal to scale with the sensor length and the vortical signal to scale as the square root of the sensor length.) Additionally, pressure pulses and pipe fluids with uniform varying temperatures should also produce signals in this configuration. These signals, i.e. signals from the acoustic pressures, the pressure pulses, and the varying temperature fluids may degrade the measurement of the vortical pressure disturbance (vortical signals).

One method of filtering the acoustic noise is to difference the signals of adjacent sensors 112. While this increases the signal to noise ratio, it would be advantageous if each sensor 112 had the ability to filter both the unsteady pressures associated with the bending modes of the pipe 104 and the acoustic noise (or pressure field).

It should be appreciated that in any of the embodiments described herein, the sensors 112 may include electrical strain gages, optical fibers and/or gratings, ported sensors, ultrasonic sensors, among others as described herein, and may be attached to the pipe by adhesive, glue, epoxy, tape or other suitable attachment means to ensure suitable contact between the sensor 112 and the pipe 104. The sensors 112 may alternatively be removable or permanently attached via known mechanical techniques such as mechanical fastener, spring loaded, clamped, clam shell arrangement, strapping or other equivalents. Alternatively, strain gages, including optical fibers and/or gratings, may be embedded in a composite pipe 104. If desired, for certain applications, gratings may be detached from (or strain or acoustically isolated from) the pipe 104 if desired. It is also contemplated that any other strain sensing technique may be used to measure the variations in strain in the pipe 104, such as highly sensitive piezoelectric, electronic or electric, strain gages attached to or embedded in the pipe 104.

It should be further appreciated that in various embodiments of the present invention, a piezo-electronic pressure transducer may be used as one or more of the pressure sensors and it may measure the unsteady (or dynamic or ac) pressure variations inside the pipe 104 by measuring the pressure levels inside the pipe 104. For example, in one embodiment of the present invention, the sensors 112 may comprise pressure sensors manufactured by PCB Piezotronics of Depew, N.Y. and/or may include integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The sensors 112 may incorporate a built-in MOSFET microelectronic amplifier to convert the high-impedance charge output into a low-impedance voltage signal. The sensors 112 may be powered from a constant-current source and can operate over long coaxial or ribbon cable without signal degradation. It should be appreciated that the low-impedance voltage signal is not affected by triboelectric cable noise or insulation resistance-degrading contaminants and power to operate integrated circuit piezoelectric sensors generally takes the form of a low-cost, 24 to 27 VDC, 2 to 20 mA constant-current supply. Most piezoelectric pressure sensors are constructed with either compression mode quartz crystals preloaded in a rigid housing, or unconstrained tourmaline crystals. These designs advantageously give the sensors microsecond response times and resonant frequencies in the hundreds of kHz, with minimal overshoot or ringing, wherein small diaphragm diameters ensure spatial resolution of narrow shock waves.

Additionally, the output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

Furthermore it is contemplated that each of the sensors 112 may include a piezoelectric sensor that provides a piezoelectric material to measure the unsteady pressures of the flow 102. The piezoelectric material, such as the polymer, polarized fluoropolymer, PVDF, measures the strain induced within the process pipe 104 due to unsteady pressure variations within the flow 102. Strain within the pipe 104 is transduced to an output voltage or current by the attached piezoelectric sensors 112. The PVDF material forming each piezoelectric sensor 112 may be adhered to the outer surface of a steel strap that extends around and clamps onto the outer surface of the pipe 112. The piezoelectric sensing element is typically conformal to allow complete or nearly complete circumferential measurement of induced strain. The sensors can be formed from PVDF films, co-polymer films, or flexible PZT sensors, similar to that described in "Piezo Film Sensors technical Manual" provided by Measurement Specialties, Inc. of Fairfield, N.J., which is incorporated herein by reference. The advantages of this technique include non-intrusive flow rate measurements, low cost, a measurement technique requires no excitation source (i.e. ambient flow noise is used as a source), flexible piezoelectric sensors can be mounted in a variety of configurations to enhance signal detection schemes (these configurations include a) co-located sensors, b) segmented sensors with opposing polarity configurations, c) wide sensors to enhance acoustic signal detection and minimize vortical noise detection, d) tailored sensor geometries to minimize sensitivity to pipe modes, e) differencing of sensors to eliminate acoustic noise from vortical signals) and higher temperatures (140 C) (co-polymers).

It should be appreciated that the present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

The Scope of the Invention

It should be further appreciated that any of the features, characteristics, alternatives or modifications described regarding a particular embodiment herein may also be applied, used, or incorporated with any other embodiment described herein. In addition, it is contemplated that, while the embodiments described herein are useful for homogeneous flows, the embodiments described herein can also be used for dispersive flows having dispersive properties (e.g., stratified flow). Although the invention has been described and illustrated with respect to exemplary embodiments thereof, the foregoing and various other additions and omissions may be made therein and thereto without departing from the spirit and scope of the present invention.

What is claimed is:

1. Apparatus, including a density meter, comprising:
a signal processor configured to:
receive signals containing information about two speed of sound measurements having two sets of data related to materials flowing within a pipe; and
process the two sets of data simultaneously and determine corresponding signals containing information about a characteristic about the materials flowing within the using a ridge point by point difference in order to cancel substantially effects of dispersion based upon the signals received.

2. Apparatus according to claim 1, wherein the signal processor is configured to receive the signals from two SONAR meters arranged in relation to the pipe, including for a density meter where the two SONAR meters arranged on two different pipes or two different sections of the pipe that have different compliances.

3. Apparatus according to claim 2, wherein the signal processor is configured to use a differential calculation based at least partly on the fact that the same materials are passing through the two SONAR meters and dispersion characteristics should be similar.

4. Apparatus according to claim 1, wherein the signal processor is configured to perform a point by point ridge subtraction in frequency so as to obtain a straightened differential k-ω plot of an acoustic ridge.

5. Apparatus according to claim 4, wherein the signal processor is configured to use a simple line fit to calculate the difference in the speed of sound between the two speed of sound measurements.

6. Apparatus according to claim 5, wherein the signal processor is configured to perform a calculation or derive certain characteristics about the materials, including a density measurement, based at least partly on the determination of the ridge point by the point difference.

7. Apparatus according to claim 1, wherein the signal processor is configured to correct for dispersion due to a variance of the materials in the pipe, including varying particle size, densities or material mixtures in the pipe.

8. Apparatus according to claim 1, wherein the signal processor is configured to correct for dispersion based at least partly on a relationship between the frequency (Hz) and a wavenumber (1/ft) related the signals received from two SONAR meters arranged in relation to the pipe.

9. Apparatus according to claim 1, wherein the signal processor is configured to determine the difference in the speed of sound between the two speed of sound measurements, which is directly proportional to the density of the materials.

10. Apparatus according to claim 1, wherein the apparatus takes the form of a density meter.

11. Apparatus according to claim 1, wherein the apparatus comprises two SONAR meters arranged in relation to the pipe and configured to provide the signals containing information about two speed of sound measurements having two sets of data related to materials within a pipe for processing by the signal processor.

12. Apparatus according to claim 1, wherein the signal processor is configured to corresponding signals containing information about the characteristic related to the materials.

13. Apparatus according to claim 1, wherein the characteristic related to the materials is density.

14. Apparatus, including a density meter, comprising:
a signal processor configured to:
receive signals containing information about two speed of sound measurements having two sets of data related to materials within a pipe; and
process the two sets of data simultaneously and determine a ridge point by point difference in order to cancel substantially effects of dispersion;
the signal processor being configured to perform a point by point ridge subtraction in frequency so as to obtain a straightened differential k-ω plot of an acoustic ridge, to use a simile line fit to calculate the difference in the speed of sounds between the two speed of sound measurements, and to perform the simple line fit before a final speed of sound calculation is done, so that errors associated with each individual linear fits to separate ridges are eliminated and so that all common mode effects are eliminated between the two speed of sound measurements and a linear fit at the end can average out any different systematic noise on each signal.

15. A method comprising:
receiving in a signal processor signals containing information about two speed of sound measurements having two sets of data related to materials within a pipe; and
processing in the signal processor the two sets of data simultaneously and determining corresponding signals containing information about a characteristic related to the materials flowing within the pipe using a ridge point by point difference to cancel substantially effects of dispersion, based upon the signals received.

16. A method according to claim 15, wherein the method comprises receiving the signals from two SONAR meters arranged in relation to the pipe, including for a density meter where the two SONAR meters arranged on two different pipes or two different sections of the pipe that have different compliances.

17. A method according to claim 16, wherein the method comprises using a differential calculation based at least partly on the fact that the same materials are passing through the two SONAR meters and dispersion characteristics should be similar.

18. A method according to claim 15, wherein the method comprises performing a point by point ridge subtraction in frequency so as to obtain a straightened differential k-ω plot of an acoustic ridge.

19. A method according to claim 18, wherein the method comprises using a simple line fit to calculate the difference in the speed of sound between the two speed of sound measurements.

20. A method according to claim 19, wherein the method comprises performing the simple line fit before a final speed of sound calculation is done, so that errors associated with each individual linear fits to separate ridges are eliminated and so that all common mode effects are eliminated between the two speed of sound measurements and a linear fit at the end can average out any different systematic noise on each signal.

21. A method according to claim 19, wherein the method comprises performing a calculation or derive certain characteristics about the materials, including a density measurement, based at least partly on the determination of the ridge point by the point difference.

22. A method according to claim 15, wherein the method comprises correcting for dispersion due to a variance of the materials in the pipe, including varying particle size, densities or material mixtures in the pipe.

23. A method according to claim 15, wherein the method comprises correcting for dispersion based at least partly on a relationship between the frequency (Hz) and a wavenumber (1/ft) related the signals received from two SONAR meters arranged in relation to the pipe.

24. A method according to claim 15, wherein the signal processor is configured to determine the difference in the speed of sound between the two speed of sound measurements, which is directly proportional to the density of the materials.

25. A method according to claim 15, wherein the method comprises using the signal processor in a density meter.

26. A method according to claim 15, wherein the method comprises arranging two SONAR meters in relation to the pipe that are configured to provide the signals containing information about two speed of sound measurements having two sets of data related to materials within a pipe for processing by the signal processor.

27. A method according to claim 15, wherein the method further comprises providing with the signal processor corresponding signals containing information about the characteristic related to the materials.

28. A method according to claim 15, wherein the characteristic related to the materials is density.

29. Apparatus comprising:
means for receiving in a signal processor signals containing information about two speed of sound measurements having two sets of data related to materials within a pipe; and
means for processing the two sets of data simultaneously and determining corresponding signals containing information about a characteristic related to the materials flowing within the using a ridge point by point difference to cancel substantially effects of dispersion, based upon the signals received.

* * * * *